(12) United States Patent
Duceppe et al.

(10) Patent No.: US 7,705,169 B2
(45) Date of Patent: Apr. 27, 2010

(54) PREPARATION OF METAL SALTS OF MEDIUM-CHAIN FATTY ACIDS

(75) Inventors: Jean-Simon Duceppe, Quebec (CA); Abdallah Ezzitouni, Quebec (CA); Christopher Penney, Quebec (CA); Boulos Zacharie, Quebec (CA)

(73) Assignee: Prometic Biosciences Inc., Quebec (CA)

( * ) Notice: Subject to any disclaimer, the term of this patent is extended or adjusted under 35 U.S.C. 154(b) by 0 days.

(21) Appl. No.: 10/565,762

(22) PCT Filed: Jul. 23, 2004

(86) PCT No.: PCT/GB2004/003182

§ 371 (c)(1),
(2), (4) Date: Jul. 7, 2006

(87) PCT Pub. No.: WO2005/012217

PCT Pub. Date: Feb. 10, 2005

(65) Prior Publication Data

US 2007/0027343 A1 Feb. 1, 2007

Related U.S. Application Data

(60) Provisional application No. 60/489,918, filed on Jul. 25, 2003.

(51) Int. Cl.
C07C 51/00 (2006.01)
(52) U.S. Cl. .................. 554/156; 562/606
(58) Field of Classification Search ........... 554/156; 562/606
See application file for complete search history.

(56) References Cited

U.S. PATENT DOCUMENTS

| 3,705,852 | A |   | 12/1972 | Fischer |
|---|---|---|---|---|
| 4,235,794 | A | * | 11/1980 | Rieber et al. ............ 554/73 |
| 5,191,097 | A |   | 3/1993 | Dynes et al. |
| 5,759,252 | A |   | 6/1998 | Edelmann et al. |
| 6,137,005 | A |   | 10/2000 | Hjoernevik |

FOREIGN PATENT DOCUMENTS

| CN | 1052846 | | 7/1991 |
|---|---|---|---|
| DE | 569 946 | | 2/1933 |
| DE | 1 494 998 | | 1/1969 |
| DE | 2 127 175 | | 12/1971 |
| DE | 2 159 347 | | 6/1972 |
| DE | 2 401 159 | | 7/1974 |
| DE | 3 403 621 | | 8/1984 |
| EP | 0 632 008 | | 1/1995 |
| EP | 0 802 248 | | 10/1997 |
| GB | 1 335 257 | | 10/1973 |
| GB | 1 408 123 | | 10/1975 |
| GB | 2 134 517 | | 8/1984 |
| RO | 115885 | * | 7/2000 |
| RO | 115885 B1 | | 7/2000 |

OTHER PUBLICATIONS

RO-115885,WPIDS, 2000-600798, 2000.*
Baileys Industrial Oil and Fat Products, vol. 2, Edible Oil and Fat Products: Oils and Oilseeds, 1996.*
Kurata et al. (Rapid Discrimination of Fatty Acid Composition..., Analytical Sciences 21, 1457-1465, 2005).*
Braun, "Die Metallseifen," 1932, pp. 13-14.
"Definition of fatty acids", IUPAC Gold Book, Jan. 25, 2008, <http://goldbook.iupac.org/F02330.html>.
Falbe et al., Rompp Chemie Lexikon, pp. 1343-1345.
Jacobson et al., "Solubility Data for Various Salts of Lauric, Myristic, Palmitic, and Stearic Acids," The Journal of Biological Chemistry, 1916, vol. 25, pp. 29-53.
Library of Congress Catalog Card No. 60-10162, Markley ed., "Salts of Fatty Acids," Fatty Acids: Their Chemistry, Properties, Production, and Uses, Part 2, 1961, pp. 746-755.

* cited by examiner

Primary Examiner—Deborah D Carr
(74) Attorney, Agent, or Firm—Saliwanchik, Lloyd & Saliwanchik

(57) ABSTRACT

A process for the preparation of metal salts of a medium-chain length monocarboxylic fatty acid comprises reacting the precursor free fatty acid, dissolved in a suitable solvent, with the appropriate metal salt. The process uses a relatively high concentration of free fatty acid as a soluble reactant and produces metal fatty acid salts at high purity and high yield at a reasonable cost.

12 Claims, No Drawings

PREPARATION OF METAL SALTS OF MEDIUM-CHAIN FATTY ACIDS

This application is a National Stage Application of International Application No. PCT/GB2004/003182, filed Jul. 23, 2004; which claims the benefit of U.S. Provisional Application No. 60/489918, filed Jul. 25, 2003.

FIELD OF THE INVENTION

This Invention relates to the preparation of metal salts of a medium-chain length monocarboxylic fatty acid.

BACKGROUND OF THE INVENTION

Medium-chain fatty acids and their metal salts are non-toxic materials which are used in the food and pharmaceutical industries. According to part 184 of the Code of Federal Regulations (CFR), the US Food and Drug Administration (FDA) has granted the medium-chain, $C_8$ fatty acid, caprylic acid or octanoic acid, a GRAS (Generally Recognized As Safe) affirmation. Similarly, according to part 172 (CFR) free fatty acids (e.g., caprylic acid, capric acid, lauric acid) and their metal salts, are recognized as safe additives for use in food. As noted by Dimitrijevic et al, Journal of Pharmacy and Pharmacology 53:149-154 (2001), the sodium salt of the medium-chain, $C_{10}$ fatty acid, capric acid or decanoic acid, is approved for human use in Sweden and Japan as an absorption enhancer for rectal drug products.

WO02183120 discloses that medium-chain fatty acids and their metal salts (especially capric acid, caprylic acid and their sodium salts) are able to induce hematopoiesis. The sodium salts of capric acid and caprylic acid, in comparison to the respective free acids, possess superior water solubility. The solubility of capric acid is 15 mg/100 g water (20° C.) whilst that of caprylic acid is 68 mg/100 g water (20° C.).

Typically, the reaction of an acid with base in an aqueous medium is rapid and straightforward, as long as the acid and base are water-soluble. The limited water-solubility of medium-chain fatty acids makes the large-scale, high-yield preparation of the metal salts of fatty acids more difficult. Emulsions and suspensions can form, with excessive frothing and foam if carbon dioxide is a byproduct of the reaction (e.g., use of bicarbonate or carbonate base).

SUMMARY OF THE INVENTION

An object of the invention is to provide a process for synthesizing a metal salt of a medium-chain fatty acid (i.e., a chain length of from six to twelve carbons). At least one free fatty acid of the appropriate length (i.e., precursor) is solubilized in solvent. The solvent may comprise one or more alcohols. Free fatty acid is reacted with at least one metal salt to produce the metal salt of the medium-chain fatty acid. The metal salt may comprise a monovalent cation (e.g., sodium, potassium) or a divalent cation (e.g., calcium, magnesium); it may be at least one metal bicarbonate or carbonate. Preferred metal fatty acid salts are sodium or potassium caprylate, and sodium or potassium caprate.

Another object of the invention is to recover the metal fatty acid salt synthesized by the aforementioned process, by precipitation and/or filtration.

Yet another object of the invention is to determine purity of the metal fatty acid salts synthesized by the aforementioned process, by separation of reaction products and/or qualification of such products.

Further aspects of the invention will be apparent to a person skilled in the art from the following description and claims, and generalizations thereto.

DESCRIPTION OF SPECIFIC EMBODIMENTS

The problem exists, of finding a method for the preparation of water-soluble medium-chain fatty acid salts from water-insoluble or sparingly soluble medium-chain free fatty acids. The metal salt products must be conveniently prepared on large scale in high purity and high yield at a reasonable cost. It has been found surprisingly that, when a concentrated solution of medium-chain fatty acid dissolved in ethanol (e.g, absolute to 95% in water) is heated and then allowed to react with almost one equivalent of bicarbonate, the metal salt product is obtained in high purity and good yield. This high purity and yield negates any difficult (on large-scale) purification by column chromatography and/or crystallization. As shown in the following Examples, purification is achieved by filtration and washing with volatile (organic) solvents.

The novel process comprises reacting the precursor free fatty acid, dissolved in a suitable solvent, with the appropriate bicarbonate or carbonate salt. The process uses a relatively high concentration of free fatty acid as a soluble reactant with a consequently small amount of foam arising from the formation of carbon dioxide. Therefore, the process allows for the convenient large-scale preparation of fatty acid salt products.

Medium-chain fatty acids refer to those monocarboxylic fatty adds having carbon chain lengths of 6 (caproic add, hexanoic acid), 8 (caprylic add, octanoic acid), 10 (capric acid, decanoic acid) and 12 (lauric add, dodecanoic acid). While even-numbered carbon atom chain lengths, and the preparation of their metal salts, constitute a preferred embodiment of this invention, it is not limited to even-numbered carbon atom chains. Odd-numbered carbon atom chains include 7 carbons (heptanoic acid), 9 carbons (nonanoic acid) and 11 carbons (undecanoic acid).

A concentration of free fatty add reactant of at least 0.5 M is preferred for synthesis; also preferred is a maximal concentration of 1.5 M. The solubility of medium-chain fatty acid is typically no more than 1.5 gm/100 g water (20° C.) for C6 to C12. In particularly preferred embodiments, the metal salt of a medium-chain fatty acid refers to the sodium or potassium salt of capric acid or caprylic acid.

The reaction temperature is preferably 50° C. to reflux (78° C.) and more preferably at reflux of 95% ethanol and 5% water solvent. Temperatures of less than 50° C. are less desirable since they reduce the speed of the reaction and result in a reduced yield of metal salt (product) relative to free fatty acid (reactant). Yields of greater than 50%, preferably greater than 60%, more preferably greater than 80%, and even more preferably greater than 90%, can be achieved.

The following Examples are presented to illustrate the invention but are not intended to limit the invention. The reaction in the Examples may be summarized by the equation below (n=4-10):

EXAMPLE 1

Sodium Decanoate (Capric Acid Sodium Salt: n=8)

To a twelve-liter three-necked flask equipped with a thermometer, mechanical stirrer, and a reflux condenser, were added decanoic acid (500 g, 2.9 mole) and absolute ethanol (5.5 L). The mixture was stirred vigorously for 5 minutes. The clear solution was then diluted with water (275 ml). Solid sodium bicarbonate (218 g, 2.6 mole) was added in one portion and the resulting suspension heated under reflux for 12 hours. At the end of the reaction the pH was observed to be neutral. The clear solution was then cooled slowly during 3 hours to 42° C. under vigorous stirring. The resulting mixture was diluted with tert-butyl methyl ether (1.1 L) and stirring was continued for an additional 4 hours. The temperature dropped to 30° C. The white precipitate was filtered under suction (water aspirator) using a polypropylene coarse glass funnel (7 L) and the wet solid was air-dried for 1.5 hours. The product was broken up into small pieces using a spatula and kept under high vacuum at 20° C. for 16 hours. The pure acid sodium salt was isolated as a white solid. Yield of product: 439 g (87%); mp=248-250° C.; $^1$HNMR ($D_2O$, 400 MHz) δ: 2.0 (t, J=7.43 Hz, 2H); 1.4 (m, 2H); 1.1 (m, 12H); 0.71 (t, J=7.04 Hz, 3H). $^{13}$C NMR ($D_2O$, 400 MHz) δ: 184.3; 38.0; 31.5; 29.1; 29.0; 28.9; 28.8; 26.3; 22.4; 13.8.

Purity of sodium decanoate was assessed by HPLC analysis.

a) Analysis of Decanoate Anion of Sodium Decanoate

Instrumentation: HPLC (Waters 600 and 717 plus) equipped with a conductivity detector (Waters 432) and a PRP-X100 resin-based ion chromatography column (150 mm×41 mm OD). The mobile phase is a mixture of 2.5% methanol in a 4 mM p-hydroxybenzoic acid solution. The pH of the final solution is adjusted to 8.5. Analysis is carried out at 40° C. under a flow rate of 2 ml/minute.

The decanoate salt peak appears at a retention time of 17 minutes. A calibration curve was used to calculate the purity of the decanoate salt in the final product.

b) Analysis of Sodium Cation of Sodium Decanoate

Instrumentation: HPLC (Waters 600 and 717 plus) equipped with a conductivity detector (Waters 431) and a Hamilton PRP-X200 resin-based ion chromatography column (250 mm×41 mm OD). The mobile phase is a mixture of 30% methanol in a 4 mM nitric acid solution. Analysis is carried out at 40° C. under a flow rate of 2 ml/minute.

The sodium cation peak appears at a retention time of 4 minutes. A calibration curve was used to calculate the sodium in the decanoate salt in the final product.

c) Identification of Unreacted Capric Acid

Instrumentation: Preparative HPLC (Waters 4000) equipped with refractive index monitor (Waters 2414) and a radial compression module (Waters 8×100). A preparative $C_{18}$ column (Nova-Pak HR 8×100) was used with a Shimadzu CR 501 chromatopac integrator. The mobile phase was prepared by mixing acetonitrile with tetrahydrofuran and water in a ratio of 5:1:4.

The unreacted capric acid peak appeared at a retention time of 7 minutes. A calibration curve was used to calculate unreacted capric acid present in the final sodium decanoate salt product.

EXAMPLE 2

Sodium Dodecanoate (Lauric Acid Sodium Salt: n=10)

The sodium salt of dodecanoic acid (lauric acid) was prepared as described in Example 1 by use of 20.0 g dodecanoic acid (100 mmole) and 8.0 g sodium bicarbonate (95 mmole). Yield of product: 19.1 g (91%); mp=244-246° C.; $^1$H NMR ($D_2O$, 400 MHz) δ: 2.04 (t, J=7.34 Hz, 2H); 1.4 (m, 2H); 1.15 (m, 16H); 0.73 (m, 3H). $^{13}$C NMR ($D_2O$, 400 MHz) 5:183.98; 38.8; 31.9; 29.5; 29.4; 29.3; 29.2; 26.7; 22.8; 14.3.

EXAMPLE 3

Sodium Hexanoate (Caproic Acid Sodium Salt: n=4)

The sodium salt of hexanoic acid (caproic acid) was prepared as described in Example 1 by use of 20.0 g hexanoic acid (172 mmole) and 14.0 g sodium bicarbonate (164 mmole). Yield of product: 21.3 g (94%); mp=232-234° C.; $^1$H NMR ($D_2O$, 400 MHz) 6:2.02 (t, J=7.43 Hz, 2H); 1.4 (m, 2H); 1.16 (m, 4H); 0.75 (t, J=6.75 Hz, 3M). $^{13}$C NMR ($D_2O$, 400 MHz) δ: 183.9; 38.3; 31.8; 26.3; 22.6; 14.1.

EXAMPLE 4

Sodium Octanoate (Caprylic Acid Sodium Salt: n=6)

The sodium salt of octanoic acid (caprylic acid) was prepared as described in Example 1 by use of 20.0 g octanoic acid (139 mmole) and 11.1 g sodium bicarbonate (132 mmole). Yield of product: 20.4 g (93%); mp=243-245° C.; $^1$H NMR ($D_2O$, 400 MHz) δ: 2.1 (m, 2H); 1.42 (m, 2H); 1.15 (m, 8H); 0.75 (m, 3H). $^{13}$C NMR ($D_2O$, 400 MHz) δ: 183.9; 38.3; 31.8; 29.5; 29.0; 26.7; 22.8; 14.3.

EXAMPLE 5

Calcium Decanoate (Capric Acid Calcium Salt: n=8)

To a one-liter three-necked flask equipped with a thermometer, mechanical stirrer, and a reflux condenser, were added decanoic acid (20.0 g, 116 mmole) and absolute ethanol (0.19 L). The mixture was stirred vigorously for 5 minutes. The clear solution was then diluted with water (30 ml). Solid calcium carbonate (5.5 g, 55 mmole) was added in one portion and the resulting white suspension heated under reflux for 12 days. Water (10 ml) was added to the reaction each day except the last one. On the last day, excess water (100 ml) was added to complete the reaction. The mixture was cooled to 45° C. (water bath) and filtered through a coarse glass funnel. This gave a white solid which was washed with absolute ethanol (50 ml), tert-butyl methyl ether (2×50 ml) and air-dried for 2 hours. The solid was then dissolved in boiling methanol (1.3 L) and the cloudy solution filtered on a Celite pad. The clear filtrate was cooled and concentrated to 300 ml. The white precipitate was filtered under suction (water aspirator) using a coarse glass funnel (1 L) and air-dried for 3 hours. The resulting solid was kept under high vacuum at 20° C. for 18 hours. The pure acid calcium salt was isolated as a snow-white solid. Yield of product: 14.0 g (63%); mp=172-76° C., $^1$H NMR ($CD_3OD$, 400 MHz) δ: 2.18 (t, J=7.63 Hz, 4H); 1.61 (m, 4H); 1.30 (m, 24H); 0.91 (t, J=7.04 Hz, 6H); $^{13}$C NMR ($D_2O$, 400 MHz) δ: 183.0, 38.0, 32.4, 30.2, 30.1, 30.0, 29.8, 26.9, 23,1, 13.9.

All modifications and substitutions that come within the meaning of the claims and the range of their legal equivalents are within their scope. Claims having "comprising" allows the inclusion of other elements to be within the scope of the claim; the invention may also be described by such claims having the transitional phrase "consisting essentially of" (i.e., allowing inclusion of another element to be within the scope of a claim if it does not materially affect practice of the invention) and the transitional term "consisting" (i.e., allowing only elements listed in a claim other than impurities or inconsequential activities which are ordinarily associated with the invention) instead of the "comprising" term. Any of these three transitions can be used to claim the invention.

It should be understood that an element described in this specification should not be construed as a limitation of the claimed invention unless it is explicitly recited in the claims. Thus, the granted claims are the basis for determining the scope of legal protection instead of a limitation from the specification which is read into the claims. In contradistinction, the prior art is explicitly excluded from the invention to the extent of specific embodiments that would anticipate the claimed invention or destroy novelty.

No particular relationship between or among limitations of a claim is intended unless such relationship is explicitly recited in the claim (e.g., the arrangement of components in a product claim or order of steps in a method claim is not a limitation of the claim unless explicitly stated to be so). All possible combinations and permutations of individual elements disclosed herein are considered to be aspects of the invention. Similarly, generalizations of the invention's description are considered to be part of the invention.

From the foregoing it would be apparent to a skilled person that the invention can be embodied in other specific forms without departing from its spirit or essential characteristics. The described embodiments should be considered only as illustrative, not restrictive, because the scope of the legal protection provided for the invention will be indicated by the appended claims rather than by this specification.

The invention claimed is:

1. A method of preparing a metal salt of a medium-chain fatty acid, wherein the method comprises solubilizing at least one free fatty acid in solvent, wherein the solvent comprises an alcohol, wherein said free fatty acid has a chain length from six to twelve carbons; and reacting said free fatty acid with at least one metal salt, wherein the metal salt comprises at least one metal bicarbonate or metal carbonate, to produce a metal fatty acid salt.

2. The method according to claim 1, wherein the metal salt comprises a monovalent cation or a divalent cation.

3. The method according to claim 2, wherein the metal salt comprises sodium or potassium.

4. The method according to claim 2, wherein the metal salt comprises calcium or magnesium.

5. The method according to claim 1, wherein the metal fatty acid salt is sodium or potassium caprylate.

6. The method according to claim 5, wherein the metal fatty acid salt is sodium caprylate.

7. The method according to claim 1, wherein the metal fatty acid salt is sodium or potassium caprate.

8. The method according to claim 7, wherein the metal fatty acid salt is sodium caprate.

9. The method according to claim 1, wherein the concentration of the free fatty acid in solvent is at least 0.5 M.

10. The method according to claim 1, further comprising recovering the metal fatty acid salt by precipitation and filtration.

11. A process for quantifying the purity of a metal fatty acid salt prepared by solubilizing at least one Free fatty acid in solvent, wherein said free fatty acid has a chain length from six to twelve carbons; and reacting said free fatty acid with at least one metal salt, to produce a metal fatty acid salt wherein the process for quantifying the purity of the metal fatty acid salt comprises separating product from reactants by High Pressure Liquid Chromatography (HPLC).

12. The method according to claim 1, further comprising isolating the metal fatty acid salt.

* * * * *